(12) United States Patent
Farquar et al.

(10) Patent No.: US 9,023,650 B2
(45) Date of Patent: May 5, 2015

(54) DNA TAGGED MICROPARTICLES

(71) Applicant: Lawrence Livermore National Security, LLC, Livermore, CA (US)

(72) Inventors: George Roy Farquar, Livermore, CA (US); Roald N. Leif, San Ramon, CA (US); Elizabeth Wheeler, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 0 days.

(21) Appl. No.: 14/070,395

(22) Filed: Nov. 1, 2013

(65) Prior Publication Data

US 2014/0057276 A1    Feb. 27, 2014

Related U.S. Application Data

(63) Continuation-in-part of application No. 13/608,962, filed on Sep. 10, 2012, now Pat. No. 8,835,178, which is a continuation of application No. 12/909,428, filed on Oct. 21, 2010, now Pat. No. 8,293,535.

(60) Provisional application No. 61/257,242, filed on Nov. 2, 2009.

(51) Int. Cl.
*G01N 21/64* (2006.01)
*G01N 33/58* (2006.01)
*C12Q 1/68* (2006.01)

(52) U.S. Cl.
CPC ............... *C12Q 1/6876* (2013.01); *C12Q 1/68* (2013.01); *G01N 33/582* (2013.01); *G01N 21/6428* (2013.01); *G01N 33/58* (2013.01); *G01N 2458/10* (2013.01)

(58) Field of Classification Search
CPC . G01N 1/00; G01N 21/6428; G01N 21/6486; G01N 31/00; G01N 33/02; G01N 21/64; G01N 33/58; G01N 33/582; C12Q 1/68
USPC ............... 436/8, 9, 15, 20, 94, 174, 181, 183; 435/6.1, 6.12; 252/408.1
See application file for complete search history.

(56) References Cited

U.S. PATENT DOCUMENTS

| | | | |
|---|---|---|---|
| 6,197,229 B1 | 3/2001 | Ando et al. | |
| 7,030,097 B1 | 4/2006 | Saltzman et al. | |
| 7,781,224 B2 | 8/2010 | Martin et al. | |
| 8,293,535 B2 | 10/2012 | Farquar et al. | |
| 8,835,178 B2 * | 9/2014 | Farquar et al. | 436/8 |
| 2002/0172717 A1 | 11/2002 | Leong et al. | |
| 2009/0221087 A1 | 9/2009 | Martin et al. | |
| 2012/0283379 A1 * | 11/2012 | Auger et al. | 524/556 |
| 2013/0052751 A1 | 2/2013 | Farquar et al. | |
| 2014/0272097 A1 | 9/2014 | Jung et al. | |

OTHER PUBLICATIONS

Udey et al (abstract). Abstracts, 67$^{th}$ Northwet Regional Meeting of the American Chemical Society, Boise, ID, United States, Jun. 24-27, 2012.*

(Continued)

*Primary Examiner* — Maureen Wallenhorst
(74) *Attorney, Agent, or Firm* — Zilka Kotab LLP

(57) ABSTRACT

A simulant that includes a carrier and DNA encapsulated in the carrier. Also a method of making a simulant including the steps of providing a carrier and encapsulating DNA in the carrier to produce the simulant.

18 Claims, 5 Drawing Sheets

(56) References Cited

OTHER PUBLICATIONS

Non-Final Office Action from U.S. Appl. No. 13/608,962 dated Jan. 8, 2013.
Final Office Action from U.S. Appl. No. 13/608,962 dated May 15, 2013.
Non-Final Office Action from U.S. Appl. No. 13/608,962 dated Oct. 21, 2013.
Udey, R.N., "Statistical Data Analyses of Trace Chemical, Biochemical, and Physical Analytical Signatures," LLNL TH-623193, Michigan State University, Feb. 28, 2013, pp. 1-236.
Venkatram, A., "An examination of the urban dispersion curves derived from the St. Louis dispersion study," Atmospheric Environment, vol. 39, Issue 21, Jul. 2005, pp. 3813-3822 (abstract only).
Chang et al., "Use of Salt Lake City Urban 2000 Field Data to Evaluate the Urban Hazard Prediction Assessment Capability (HPAC) Dispersion Model," 2005 American Meteorological Society, Apr. 2005, pp. 485-501.
Shea et al., "The BioWatch Program: Detection of Bioterrorism," Congressional Research Service Report No. RL 32152, Nov. 19, 2003, pp. 1-19.
Final Office Action from U.S. Appl. No. 13/608,962 dated Feb. 18, 2014.
Notice of Allowance and Fee(s) Due from U.S. Appl. No. 13/608,962 dated May 20, 2014.

\* cited by examiner

DNA TAGGED MICROPARTICLES

RELATED APPLICATIONS

The present application is a continuation-in-part of U.S. application Ser. No. 13/608,962, filed on Sep. 10, 2012, entitled "Bio-Threat Microparticle Simulants", now U.S. Pat. No. 8,835,178, issued on Sep. 16, 2014, which is a continuation of U.S. Pat. No. 8,293,535, issued on Oct. 23, 2012, which is a non-provisional application claiming priority to U.S. Provisional Patent Application No. 61/257,242 filed Nov. 2, 2009, from all of which priority is claimed, and the entire contents and disclosures of which are hereby incorporated by reference herein.

The United States Government has rights in this invention pursuant to Contract No. DE-AC52-07NA27344 between the United States Department of Energy and Lawrence Livermore National Security, LLC for the operation of Lawrence Livermore National Laboratory.

FIELD OF THE INVENTION

The present invention relates to testing and more particularly to safe and effective stimulants for testing.

BACKGROUND

U.S. Pat. No. 7,781,224 issued Aug. 24, 2001 to Sue I. Martin et al titled "Safe Biodegradable Fluorescent Particles," assigned to Lawrence Livermore, National Security, LLC., provides the following state of technology information:

The present invention provides a "safe" fluorescent particle for a variety of applications. The particle comprises a non-biological, biodegradable carrier and natural fluorophores encapsulated in the non-biological, biodegradable carrier. In some embodiments the particle is used as a simulant for mimicking the fluorescence properties of microorganisms. However, the particle need not mimic the fluorescent characteristics of a microorganism, rather it can be incorporated into one or more natural fluorophores as a means for fluorescence detection. Single or combinations of fluorophores are encapsulated to produce a desired fluorescent effect such as particles that fluoresce at 370 nm maxima. The particles can therefore be tuned to the excitation wavelength of a fluorescence detector.

One application for these particles is their use in aerosol studies, such as large scale air dispersal to track particulate migration over vast areas, or for urban particle dispersion studies. Currently, researchers performing these studies rely on air dispersion models and gas tracer tests to determine the movement and flow of aerosols in urban environments such as in cities—around and through occupied buildings—because "safe" particles are not available. These particles would provide those safety benefits. Furthermore, these particles could be designed with the appropriate density and perhaps shape of a microorganism to mimic the aerodynamic movement of a microorganism.

An example of aerosol study is described in the article, "An examination of the urban dispersion curves derived from the St. Louis dispersion study" by Akula Venkatram in *Atmospheric Environment* 39 (2005) 3813-3822, which describes the St. Louis study conducted over the period 1963-1965. The study consisted of a series of 26 daytime and 16 evening experiments in which fluorescent zinc cadmium sulfide particles were released near ground level at two different locations under a variety of meteorological conditions. During the first year of the experiments, the release was at ground level in a relatively open area in a park located west of the downtown area. In the second year, the tracer was released from the top of a three-story building surrounded by trees and similar buildings. The main downtown area, consisting of buildings with an average height of 40 m, was about 5 km away from both release locations." The disclosure of the article, "An examination of the urban dispersion curves derived from the St. Louis dispersion study" by Akula Venkatram in *Atmospheric Environment* 39 (2005) 3813-3822 is incorporated herein by this reference.

Another example of aerosol study is described in the article, "Use of Salt Lake City URBAN 2000 Field Data to Evaluate the Urban Hazard Prediction Assessment Capability (HPAC) Dispersion Model" by Joseph c. Chang in *Journal Of Applied Meteorology* pages 485-501 (2005), which provides the following background about the study: "The potential impacts of the atmospheric release of chemical, biological, radiological, and nuclear (CBRN) or other hazardous materials are of increasing concern. Hazardous releases can occur due to accidents, such as the release of toxic industrial chemicals in Bhopal, India, in 1984 (e.g., Sharan et al. 1996) and the Chernobyl nuclear power plant disaster in the Ukraine in 1986 (e.g., Puhakka et al. 1990). They can also occur as an unintentional result of military actions, such as the U.S. destruction of rockets with chemical warheads at Khamisiyah, Iraq, after the 1991 Gulf War (Winkenwerder 2002). More recently, terrorist incidents in urban settings, such as the events on 11 Sep. 2001 in New York City, N.Y., and Washington, D.C., and military conflicts dramatically raise concerns for the possibility of mass casualties." The disclosure of the article, "Use of Salt Lake City URBAN 2000 Field Data to Evaluate the Urban Hazard Prediction Assessment Capability (HPAC) Dispersion Model" by Joseph c. Chang in *Journal Of Applied Meteorology* pages 485-501 (2005) is incorporated herein by this reference.

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

Conducting atmospheric releases in order to challenge detector sensor networks poses unique challenges. With the increasing use of biosensors for the detection of threat agents there is a growing need for a universal biosimulant. The universal simulant needs to have several properties to allow for real world evaluation of biodetector and collection networks. First, the material must be able to be collected and trigger the detector. Second, the simulant must be safe to release in an environment where workers and the public will be exposed to the material. Third, the material must be able to have controllable aerosol properties, such as charge and physical or aerodynamic size. The invention details a low cost, safe, individually designed particle for the use in testing biosensor networks.

The present invention provides a microsphere/microparticle simulant comprising a carrier and DNA encapsulated in the carrier. The present invention has all of the desired properties for a universal simulant. Not only will the universal simulant be able to test and evaluate single detectors it will be optimal for the validation of atmospheric release models with multiple sensors. Currently a release study with a single simulant requires a costly experiment for a single release location. If multiple release locations are desired multiple studies must be conducted to allow each release location and transport pathway to be uniquely identified. By using Applicants' new DNA containing biosimulant multiple releases can occur simultaneously. This is accomplished by modifying the unique DNA sequence for the release material. Using unique DNA allows for a near limitless variety of unique particle identifiers.

The microsphere simulant can be used as challenge-test standards for determining sensitivity of detection technologies. The microsphere simulant can be used for large-scale air current deployments or tests for determining the movement and distribution of particles in urban environments. The microsphere simulant can be labeled to distinguish between "test" microspheres and background microorganisms/organic particles. The microsphere simulant can be used as a calibration standard for bio-detectors. The microsphere simulant can be used to train personnel to operate bio-detectors. Surface properties, such as hydrophobicity and surface charge, can be tuned/altered for various applications. The microsphere simulant provides a universal simulant that can be used for field aerosol studies, mock biowarfare training, training for rapid assessment of bioweapons labs, calibrating detection equipment, and other uses.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

Other aspects and embodiments of the present invention will become apparent from the following detailed description, which, when taken in conjunction with the drawings, illustrate by way of example the principles of the invention.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION

Figure 1:
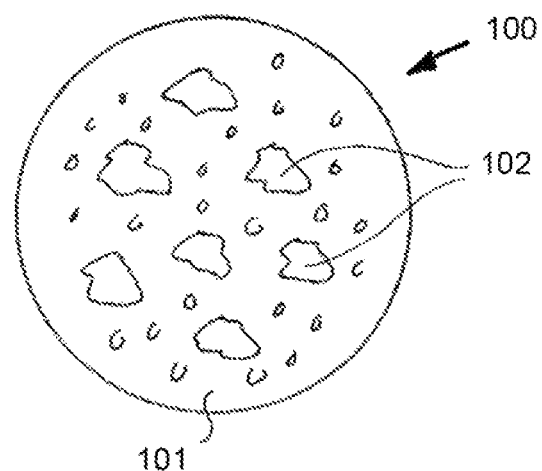
FIG. 1 illustrates a microsphere containing DNA strand and Gluconodelta-lactone (GDL).

Referring to the drawings, to the following detailed description, and to incorporated materials, detailed information about the invention is provided including the description of specific embodiments. The detailed description serves to explain the principles of the invention and is not meant to limit the inventive concepts claimed herein. The invention is susceptible to modifications and alternative forms. The invention is not limited to the particular forms disclosed. The invention covers all modifications, equivalents, and alternatives falling within the spirit and scope of the invention as defined by the claims. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified.

As used herein, the term "about" when combined with a value refers to plus and minus 10% of the reference value. For example, a length of about 1000 nm refers to a length of 1000 nm±100 nm, a temperature of about 50° C. refers to a temperature of 50° C.±5° C., etc.

The January/February 2002 issue of Science & Technology Review, in an article titled "Rapid Field Detection of Biological Agents," describes two systems to rapidly detect and identify biological agents, including pathogens such as anthrax and plague. The systems are the Handheld Advanced Nucleic Acid Analyzer (HANAA) and the Autonomous Pathogen Detection System (APDS). About the size of a brick, the HANAA biodetection system can be held in one hand and weighs less than a kilogram. The system was designed for emergency response groups, such as firefighters and police, who are often first on the scene at sites where bioterrorism may have occurred. Each handheld system can test four samples at once-either the same test on four different samples or four different tests on the same sample. HANAA can provide results in less than 30 minutes, compared with the hours to days that regular laboratory tests typically take. To detect the DNA in a sample, a synthesized DNA probe tagged with a fluorescent dye is introduced into the sample before it is inserted into the heater chamber. Each probe is designed to attach to a specific organism, such as anthrax or plague. Thus, the operator must have an idea of what substances might be involved. "The system doesn't test for all unknowns," says Langlois. "A responder has to decide what kinds of pathogens to test for ahead of time and set up the system accordingly." If that organism is present in the sample, the probe attaches to its DNA, which is then amplified during the PCR process, releasing the fluorescent tag. HANAA measures the sample's fluorescence and the presence (or absence) of the targeted organism. Whereas HANAA can be handcarried to sites at which an attack is suspected to have happened, the APDS is stationed in one place for continuous monitoring and is designed to work much like a smoke detector, but for pathogens. When fully developed, the APDS could be placed in a large area such as an airport, a stadium, or a conference hall. The system will sample the air around the clock and sound an alarm if pathogens are detected. The disclosure of the article titled "Rapid Field Detection of Biological Agents," in the January/February 2002 issue of Science & Technology Review is incorporated herein by this reference.

The October 2004 issue of Science & Technology Review, in an article titled "Detecting Bioaerosols When Time is of the Essence," states that Livermore researchers received seed funding from the Laboratory Directed Research and Development Program to develop an instrument that counters bioterrorism by providing a rapid early warning system for pathogens, such as anthrax. That instrument, the Autonomous Pathogen Detection System (APDS), is now ready for deployment to better protect the public from a bioaerosol attack, and the development team has been honored with a 2004 R&D 100 Award. In September 2003, APDS passed a series of pathogen exposure tests at a high-containment laboratory at the Dugway Proving Ground in Utah. In these trials, the system clearly demonstrated that it could detect real pathogens and confirm the identifications with a fully automated second assay method. APDS units were also deployed at the Albuquerque Airport in New Mexico and at a Washington, DC, Metro station, where they provided continuous monitoring for up to seven days, unattended. The system can be adapted for situations where environmental or clinical pathogens require monitoring. For example. APDS could test for mold or fungal spores in buildings or for the airborne spread of contagious materials in hospitals. It also could identify disease outbreaks in livestock transport centers or feedlots. The disclosure of the article titled "Detecting Bio-aerosols When Time is of the Essence," in the October 2004 issue of Science & Technology Review is incorporated herein by this reference.

The evaluation of different biofluorescence detectors as tools to detect biological attack is currently difficult due to the lack of a single, common standard with which to compare the different instruments. Biological organism stimulants present substantial drawbacks in that they are difficult to transport and aerosolize without damaging them, exposure to them presents a health risk, and they have a tendency to agglomerate, which makes their aerosolization difficult to perform reliably. Furthermore, they have a short shelf life, they are not conveniently disposable, their use requires extensive training, any equipment exposed to them requires bleach or other bactericides/sporicides for cleaning, they are difficult to manufacture, and many aspects of their growth and handling affect their final state. Therefore, biological organisms are not optimal evaluation, calibration, and training standards for biofluorescence instruments. They are, however, fluorescent in the precise manner of a microorganism (obviously), which is ultimately necessary for a test agent or surrogate.

Conducting atmospheric releases in order to challenge detector sensor networks poses unique challenges. With the increasing use of biosensors for the detection of threat agents there is a growing need for a universal biosimulant. The universal simulant needs to possess several properties to allow for real world evaluation of biodetector and collection networks. First, the material must be able to be collected and trigger the detector. Second, the simulant must be safe to release in an environment where workers and the public will be exposed to the material. Third, the material must be able to have controllable aerosol properties, such as charge and physical or aerodynamic size.

The present invention incorporates all of the desired properties. Not only will the universal simulant be able to test and evaluate single detectors it will be optimal for the validation of atmospheric release models with multiple sensors. Currently a model study with a single simulant requires a costly study for a single release location. If multiple locations are desired multiple studies must be conducted. By using Applicants' new DNA containing food safe material multiple releases can occur simultaneously. This is accomplished by modifying the unique DNA sequence for the release material. Using unique DNA allows for a near limitless variety of unique particle codes.

Microsphere Composition

According to one embodiment, a microsphere comprises a carrier and at least one DNA barcode encapsulated in the carrier. As used herein in various approaches, a microsphere may also be referred to as a microsphere simulant and/or a microparticle.

In some approaches, the morphology of the carrier may be spherical or substantially spherical, non-spherical (e.g. elliptical, tubular, etc.), irregular etc. In other approaches, the size of carrier may be between about 1 nm to about 100 μm.

In preferred approaches, the carrier may comprise a non-toxic material. In some approaches, the carrier may comprise a material that is non-toxic to at least one of: humans, animals (domesticated animals, wild animals, etc.), the environment, etc. Suitable carrier materials non-toxic to humans and/or animals may include, but are not limited to, a non-mutagenic material; a non-carcinogenic material; a non-radiological material; a material that is not harmful, hazardous, poisonous or otherwise deleterious to the health of humans and/or animals; a biocompatible ingestible material (e.g. a material suitable and/or intended to be swallowed/ingested by humans and/or animals without eliciting any undesirable local or systemic effects in humans and/or animals upon ingestion), etc. Additionally, suitable carrier materials non-toxic to the environment may include materials that are non-hazardous, non-poisonous or otherwise do not have a negative/deleterious impact on an ecosystem (e.g. an interacting system of a biological community including but not limited to plants, mammals, reptiles, fish, microbial communities, etc.) and its non-living environmental surroundings (e.g. soil, water, air, man-made structures, etc.). For instance, in some approaches, suitable materials non-toxic to the environment may be materials that are biodegradable (e.g. subject to degradation over a period of time due to exposure by biological and/or environmental conditions such as sunlight, fluids, temperature, naturally occurring microorganisms such as bacteria, etc.).

In one particular approach the non-toxic carrier material may comprise a biological material and/or a non-biological material. In another approaches, the non-toxic carrier material may comprise a carbohydrate such as maltodextrin, glucono-delta-lactone, or other suitable carbohydrate as would be understood by one having skill in the art upon reading the present disclosure.

In yet another approach, the non-toxic carrier material may be at least one of a food, a food additive, a FDA approved food additive, a color additive, and a FDA approved color additive. The term "food" may refer to any synthetic and/or naturally occurring raw, cooked, or processed edible/ingestible substance suitable and/or intended, in whole or in part, for human and/or animal consumption, in some embodiments. Additionally, a food additive may refer to any synthetic and/or naturally occurring substance which may result, or may reasonably be expected to result, directly or indirectly, in becoming a component of food and/or otherwise affecting the characteristics of food, in various embodiments. Further, in numerous embodiments, a color additive may refer to a dye, pigment or other such substance made by a synthetic process, extracted, isolated, or otherwise derived, with or without intermediate or final change of identity, from a vegetable, animal, mineral, or other source and that, when added or applied to a food, is capable (alone or through reaction with another substance) of imparting a color thereto. Moreover, a FDA approved additive, whether a food additive or a color additive, may refer, in some embodiments, to an additive subject to approval by the United States Food and Drug Administration (FDA) as being generally regarded as safe (e.g. not harmful under the intended conditions of use).

In a further approach, the non-toxic carrier material may be a material selected from a group consisting of: a carbohydrate, a food, a food additive, a FDA approved food additive, a color additive, a FDA approved color additive, a protein, a vitamin, talc, silica, an antacid, and a combination thereof.

As noted above, the microsphere comprises at least one DNA barcode encapsulated in the carrier. As used herein, a DNA barcode refers to a synthetically produced nucleic acid. In some approaches, the at least one DNA barcode encapsulated in the carrier may comprise between about 80 to about 150 bases.

In various approaches, the DNA barcode may comprise a known sequence. For example, in one embodiment, the sequence of the DNA barcode may comprise a signature associated with threat agents such as pathogens, hazardous and/or toxic chemical, biological, radiological and nuclear materials, etc. and other threat agents as would be understood by one having ordinary skill in the art upon reading the present disclosure. However, in other embodiments, the sequence of the DNA barcode may be exclusive of signatures associated with threat agents. In more embodiments, the sequence of the DNA barcode may be exclusive of signatures associated with a material/substance/particle that is naturally occurring in the environment, such as naturally occurring spores. Conversely, in even more embodiments, the sequence of the DNA may include signatures associated with a materials/substances/particles naturally that is occurring in the environment. In still more embodiments, the at least one DNA barcode may comprise a sequence configured to activate/trigger a hand held diagnostic test.

In exemplary approaches, the at least one DNA barcode comprises a unique sequence. This is advantageous where a first carrier encapsulating a first DNA barcode and a second carrier encapsulating a second DNA barcode are released in the same physical location and/or locations having at least partially overlapping perimeters and/or areas. For instance, collection and/or subsequent identification of the released carriers as being one of the first carrier or one of the second carrier may be facilitated where the first DNA barcode and the second DNA barcode each have unique sequences, i.e. the sequence associated with the first DNA barcode is different that the sequence associated with the second DNA barcode. For DNA barcode's comprising 100 bases, there are approximately $10^{60}$ unique combinations.

In further approaches, the microsphere may also comprise an additional material (a material other than the at least one DNA barcode), where the additional material is encapsulated in the carrier. The additional material may be selected from a group consisting of: a fluorophore, a protein, an immunoassay trigger, an isotope marker, a chemical signature, a sunscreen material, and combinations thereof, in various approaches.

In one exemplary approach, the additional material may comprise a fluorophore such as tryptophan. In another approach, the additional material may be configured to alter one or more properties of the carrier including but not limited to solubility, density, charge, size, morphology, etc. and other such properties as would be understood by one having skill in the art upon reading the present disclosure.

Microsphere Production

Several methods can be used to produce microsphere particles from liquid solution. The methods discussed herein focus on aerosolizing the solution and drying the resulting aerosol with a desiccant dryer. The test results discussed focus on the use of an ink jet printer to produce the initial droplets of biosimulant material. This method is used to produce a liquid droplet with reproducible size distributions. Other methods to aerosolize the material are also possible to generate the particles. Other aerosol production methods include salter and collision nebulizers for solution aersolization. The resulting liquid droplets are dried with a desiccant dryer and collected in a chamber or particle impactor. Large quantities of particles may be dried by other methods such as a spray dryers or low humidity counter flow apparatus.

Figure 7:
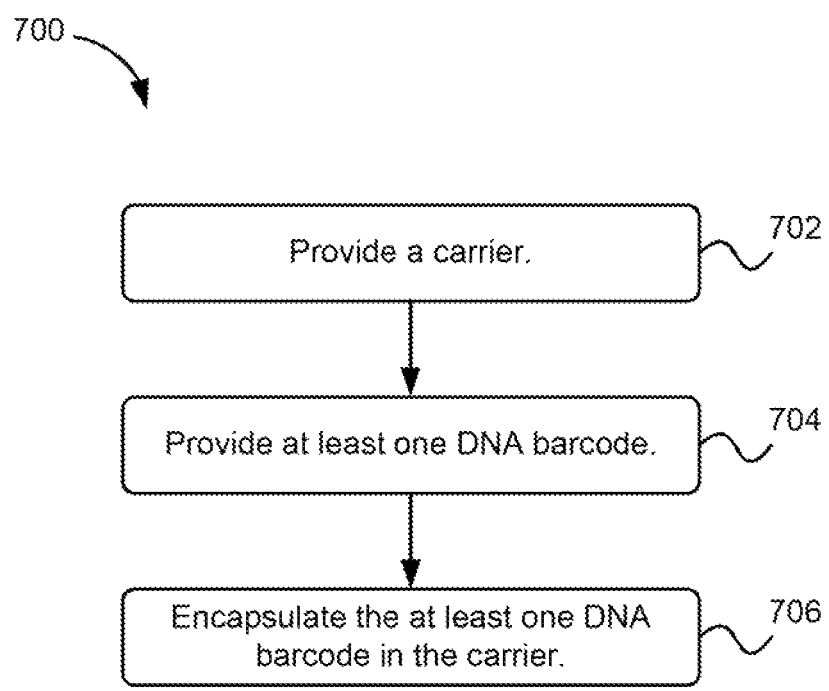
FIG. 7 illustrates a method, according to one embodiment.

FIG. 7 depicts a method 700 for forming a microsphere, such as those described herein and shown in the other FIGS., according to an exemplary embodiment. The method 700 may be carried out in any desired environment. Moreover, more or less operations than those shown in FIG. 7 may be included in method 700, according to various embodiments. It should also be noted that any of the aforementioned features may be used in any of the embodiments described in accordance with this method and others disclosed herein.

As shown in FIG. 7, the method 700 includes providing a carrier comprising a non-toxic material. See operation 702. In some approaches, the non-toxic material may be non-toxic to at least one of: humans, animals (domesticated animals, wild animals, etc.), the environment, etc. In another approach the non-toxic material may be a biological material and/or a non-biological material. In yet another approach, the non-toxic material may be selected from a group consisting of: a carbohydrate, a food, a food additive, a FDA approved food additive, a color additive, a FDA approved color additive, a protein, a vitamin, talc, silica, an antacid, and a combination thereof.

The production of the microspheres with FDA approved food product allows for the ability of ingestion of the material when it is aerosolized, in exemplary approaches. Water soluble food material such as GDL poses minimal risk for inhalation and ease of sample handling in the production process. By using water based material no organic solvents are needed greatly reducing any potential health and safety issues.

As also shown in FIG. 7, the method 700 includes providing at least one DNA barcode. See operation 704. In one approach, the at least one DNA barcode encapsulated in the carrier may comprise between about 80 to about 150 bases. In another approach, the DNA barcode may comprise a sequence that includes or excludes signatures associated with threat agents, and/or that includes or excludes signatures associated with a material/substance/particle that is naturally occurring in the environment. In yet another approach, the at least one DNA barcode may comprise a sequence configured to activate/trigger a hand held diagnostic test.

The method 700 additionally includes encapsulating the at least one DNA barcode in the carrier. See operation 706. In one approach, at least two DNA barcodes may be encapsulated in the carrier. In various approaches, these at least two encapsulated DNA barcodes may comprise sequences that are partially or completely the same. In other approaches, these at least two encapsulated DNA barcodes may comprise sequences that are partially or completely different.

In some embodiments, the method 700 may further include forming the carrier and the at least one DNA barcode encapsulated therein into droplets, and aerosolizing the droplets.

In another embodiment, the method 700 may optionally include providing an additional material and encapsulating the additional material in the carrier. The additional material may be selected from a group consisting of: a fluorophore, a protein, an immunoassay trigger, an isotope marker, a chemical signature, a sunscreen material, and combinations thereof, in exemplary approaches.

In further approaches, the composition of the carrier material may altered in order to tune one or more of the following properties of the carrier: density, morphology, solubility, size, charge, number of copies of the DNA barcode in the carrier, etc. or other such property as would be understood by one having skill in the art upon reading the present disclosure.

In yet another embodiment, the method 700 may further include providing a second carrier comprising a second non-toxic material, and encapsulating at least one unique DNA barcode in the second carrier. In some approaches, the first and second non-toxic materials associated with the first and second carriers, respectively, may be the same or different. In other approaches, the at least one unique DNA barcode encapsulated in the second carrier may be the same or different than the at least one unique DNA barcode encapsulated in the first carrier.

Any of the methods, microspheres/microparticles, systems, etc. described above, taken individually or in combination, in whole or in part, may be included in or used to make one or more systems, products, etc. In addition, any of the features presented herein may be combined in any combination to create various embodiments, any of which fall within the scope of the present invention. Following are several examples of general and specific embodiments.

EXAMPLES

The illustrative, non-limiting examples described below refer to microspheres 100 that include a carrier 101 comprising a non-toxic food product, and DNA 102 encapsulated in the carrier 101, as shown in FIG. 1. As an option, the microsphere 100 of FIG. 1 may be implemented in conjunction with features from any other embodiment listed herein, such as those described with reference to the other FIGS. Of course, the microsphere 100 and others presented herein may be used in various applications and/or in permutations which may or may not be specifically described in the illustrative embodiments listed herein. Further, the microsphere 100 presented in FIG. 1 may be used in any desired environment.

As discussed above, microspheres 100 may be produced by combining DNA 102 a carrier 101 material. The microspheres are produced by dissolving the carrier material and DNA in an aqueous solution and aerosolizing the resulting solution. The material is aerosolized to break the solution into small droplets. The size of the initial droplet and initial concentration of the solution dictates the final particle size. Larger droplets and higher concentration solutions will produce larger particle sizes. The aerosols are dried with a drying apparatus and the microspheres are collected in a collection chamber.

The specific experiments/examples described below refer to the formation of a microsphere via dissolution of a carrier material 101 comprising at least 10% Glucono-delta-lactone (GDL), and trigger DNA 102 in an aqueous solution. Furthermore, in the experiments described below, the trigger DNA 102 consists of ~100 DNA bases of thermotoga maritime. With 100 DNA bases and 4 possible substitutions for each base the maximum theoretical total number of unique combinations is $4^{100}$ (1.6 e 60). The resulting solution is divided up into droplets with an inkjet print-head or other aerosol production method and the water is removed to produce the simulant. The resulting particle is a safe, size selectable biosimulant containing DNA. By changing the concentration of the GDL or droplet size the size of the dried biosimulant can be selected.

It is important to note that the examples provided herein are not meant to be limiting in any way, but rather solely provide illustrative embodiments of the present invention.

Example 1

Production of Microspheres with a FDA Food Additive and DNA

Glucono-delta-lactone (GDL), a FDA approved kosher certified food additive, was used as the carrier material for the microsphere production. Aqueous solutions of 15% GDL were combined with known amounts of DNA. The aqueous solution was aerosolized with an inkjet printer and the resulting particles were dried with a desiccant dryer. The dried particles were collected on a particle impactor. The results from all production tests at this solution concentration show a size distribution centered at ~1.75 microns. The particles produced contained DNA in the target size range and had a spherical morphology. The size was measured with an aerosol particle sizer and the spherical morphology was confirmed with SEM images.

The mean microsphere size increases linearly with concentration of GDL. This is important, as it shows that the GDL microsphere size may be tailored to the application of interest. As we are interested in producing microspheres between 1 and 5 μm in diameter, we chose 15% GDL as the ideal starting solution to produce microspheres with the desired properties. It is also possible to alter the microsphere size by altering the initial aqueous droplet size. The resulting particle is a safe, size selectable biosimulant containing DNA.

The microsphere simulant 100 can be used as challenge-test standards for determining sensitivity of detection technologies. The microsphere simulant 100 can be used for large-scale air current deployments or tests for determining the movement and distribution of particles in urban environments. The microsphere simulant 100 can be labeled to distinguish between "test" microspheres and background microorganisms/organic particles. The microsphere simulant 100 can be used as a calibration standard for bio-detectors. The microsphere simulant 100 can be used to train personnel to operate biodetectors. Surface properties, such as hydrophobicity and surface charge, can be tuned/altered for various applications. The microsphere simulant 100 provides a universal simulant that can be used for field aerosol studies, mock biowarfare training, training for rapid assessment of bioweapons labs, calibrating detection equipment and other uses.

Figure 2:
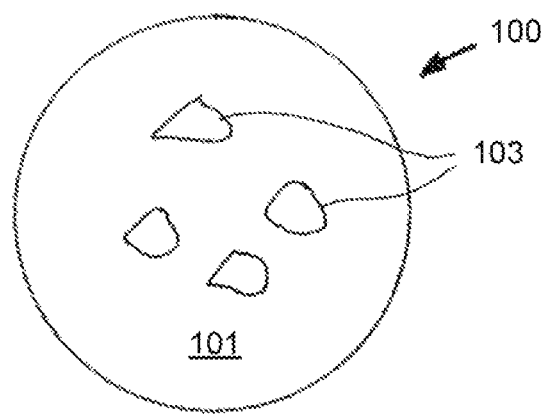
FIG. 2 illustrates a microsphere containing antibody trigger and GDL.

As illustrated in FIG. 2, DNA and antibody trigger 103 is combined with carrier material to produce microspheres stimulants. The microsphere stimulant is also generally designated by the reference numeral 100 in FIG. 2. The incorporation of the antibody trigger 103 allows the biosimulant 100 to trigger immuno assay detectors. The antibody trigger 103 is added to an aqueous solution of food safe material (currently GDL) or other carrier 101. The resulting solution is aerosolized and dried to form antibody trigger microspheres. It is critical to select the antibody trigger and antibody to take into account any health risks when the particle is released. Many natural antibody triggers such as proteins can cause allergic reactions and this must be taken into account when the trigger material is selected. Antibodies can be produced for a large range of target material ranging from explosives to bovine serum albumin. This diversity of antibodies allows for a large range of potential antibody trigger chemicals. The concentration of antibody trigger and carrier can be easily modified to change both the size of the final particle tuned to select the desired properties for a given experiment.

The microsphere simulant 100 illustrated in FIG. 2 can be used for large-scale air current deployments or tests for determining the movement and distribution of particles in urban environments. The microsphere simulant 100 can be labeled to distinguish between "test" microspheres and background microorganisms/organic particles. The microsphere simulant 100 can be used as a calibration standard for bio-detectors. The microsphere simulant 100 can be used to train personnel to operate bio-detectors. Surface properties, such as hydrophobicity and surface charge, can be tuned/altered for various applications. The microsphere simulant 100 provides a universal simulant that can be used for field aerosol studies, mock biowarfare training, training for rapid assessment of bioweapons labs, calibrating detection equipment, and other uses.

Figure 3:
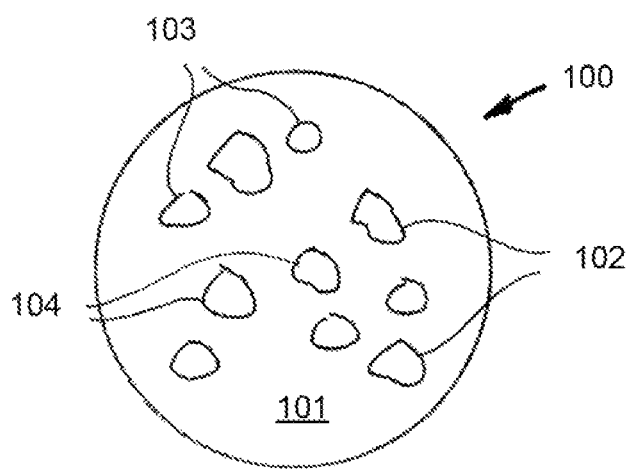
FIG. 3 illustrates a microsphere containing DNA, antibody trigger, fluorophore and GDL.

As illustrated in FIG. 3, DNA 102 and antibody triggers 103 and fluorescent molecules 104 are combined with a carrier 101 to produce microspheres stimulants 100. Antibody trigger fluorescent molecules and DNA are added to an aqueous solution of food safe material (currently GDL) or other carrier. By adding multiple fluorescent molecules a unique and tunable fluorescence signal can be achieved. The microsphere simulant 100 illustrated in FIG. 3 can be used for large-scale air current deployments or tests for determining the movement and distribution of particles in urban environments. The microsphere simulant 100 can be labeled to distinguish between "test" microspheres and background microorganisms/organic particles. The microsphere simulant 100 can be used as a calibration standard for bio-detectors. The microsphere simulant 100 can be used to train personnel to operate biodetectors. Surface properties, such as hydrophobicity and surface charge, can be tuned/altered for various applications. The microsphere simulant 100 provides a universal simulant that can be used for field aerosol studies, mock biowarfare training, training for rapid assessment of bioweapons labs, calibrating detection equipment, and other uses.

Figure 4:
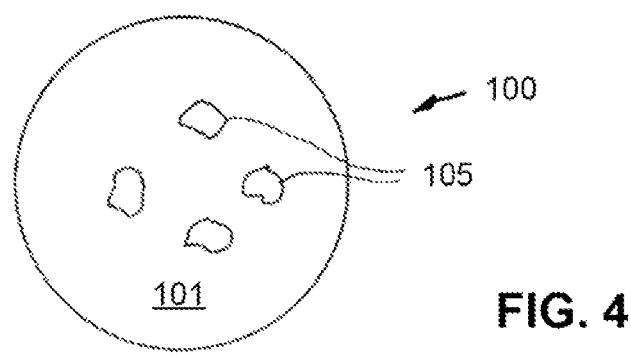
FIG. 4 illustrates a microsphere containing material to control particle transit properties.

As illustrated in FIG. 4, materials to alter the particle transport properties 105 are combined with a carrier to produce microspheres 100. Additives are added to a solution of carrier material and the resulting solution is used to produce microspheres. Properties such as charge and density greatly alter aerosol transport properties. By adding material to alter these properties a highly tunable particle can be produced to simulate a natural particle or a threat agent. Being able to reproduce the transport properties of aerosols will allow for more detailed studies of atmospheric release of pollutants and threat materials.

Figure 5:
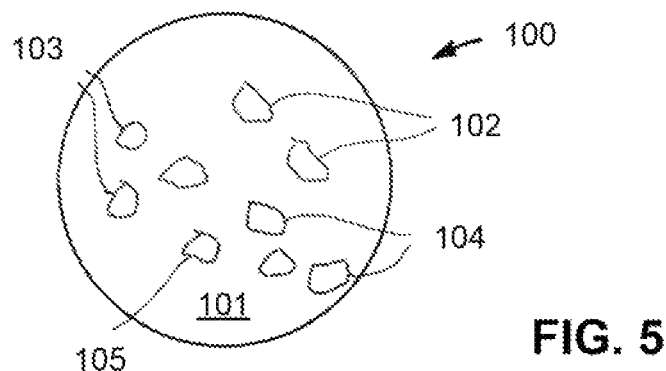
FIG. 5 illustrates a microsphere containing multiple additives combined in a single microsphere.
Figure 6:
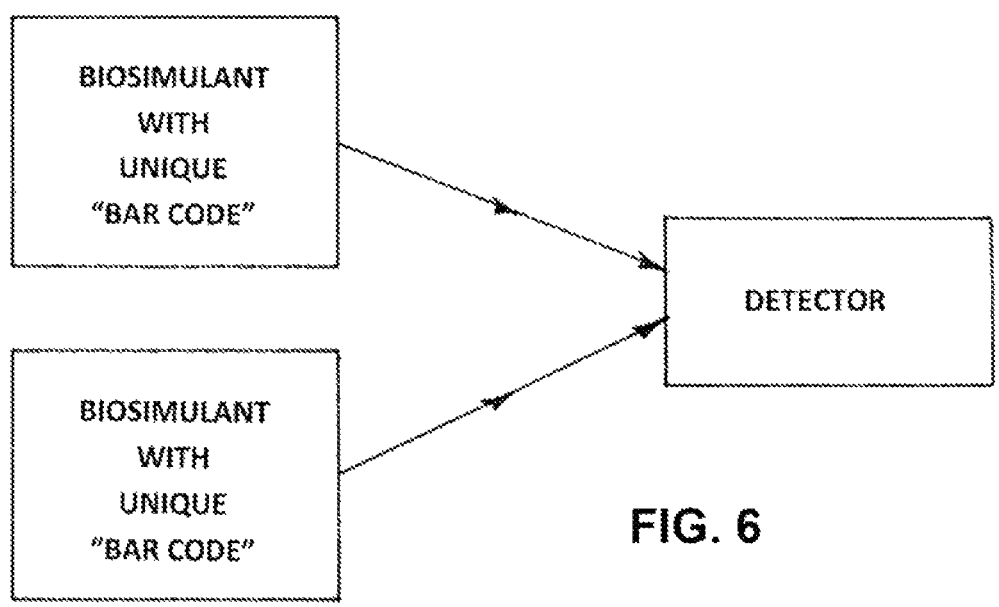
FIG. 6 illustrates how multiple microspheres, each containing unique DNA, enables for simultaneous releases during a single event.

As illustrated in FIG. 5, microspheres with DNA 102, antibody triggers 103, fluorophore 104, and materials 105 to control particle transit properties are combined with a carrier to produce microspheres 100. Antibody trigger, fluorescent molecules, additives to control transport properties and DNA are added to an aqueous solution of food safe material (currently GDL) or other carrier. The resulting solution is converted into microspheres.

Multiple varieties of DNA containing microspheres FIG. 1 are produced and simultaneously released to test bio detector networks. Current testing is limited to a small number of testing agents. By using the unique properties and DNA signature for test particles, multiple simultaneous test release can be achieved. This allows for great cost savings and rapid incorporation of real word data into modeling simulations.

Example 2

Glucono-delta-Lactone (GDL) a FDA approved kosher certified food additive was used as the carrier material for the microsphere production. Aqueous solutions of 15% GDL were combined with known amounts of DNA. Two sequences of DNA from thermotoga maritime were incorporated into two sets of microsphere particles. The aqueous solution was aerosolized with an inkjet printer. The resulting aerosol was collected and analyzed with PCR. The experiments showed that the resulting aerosol droplets can be identified with PCR.

The trigger DNA consists of ~100 DNA bases of thermotoga maritime. With ~100 DNA bases and 4 possible substitutions for each base the maximum theoretical total number of unique combinations is $4^{100}$ (1.6 e 60).

Applications and Uses

Embodiments of the present invention may be used in a wide variety of applications including but not limited to those described below.

Aerosol Transport Studies

In various approaches, embodiments of the present invention may be used for aerosol transport studies in indoor environments. One of the most overlooked threats to human health is poor indoor air quality. Various air pollutants exist indoors, including biological pollutants (molds, bacteria, viruses, pollen, animal dander, dust mites, etc.), secondhand smoke, combustion pollutants, and other chemicals (formaldehyde, asbestos, radon, etc.). These contaminants "pool" in spaces with inadequate ventilation. As a result, the quality of indoor environments can suffer, with detrimental effects on human health or even a building's structural integrity.

Moreover, poor heating and/or air conditioning (HVAC) systems in indoor ventilation environments may also affect building occupants' comfort and health. For instance, building occupants in one quadrant often may be too hot while others located in another quadrant may be too cold.

Conventional products used to track particulate migration and/or validate air transport models, such as natural and genetically modified spores, are typically expensive to produce and face significant regulatory and public perception barriers to release in public places. Additionally, once released, these spores must be removed, making the release site temporarily unavailable (up to several days) and limiting additional testing. For instance, after a traditional release using *Bacillus subtilis* or *Bacillus thuringensis* spores, the area must be decontaminated prior to a second release, otherwise, there is no way to differentiate whether the detected spores were from the first or second release.

Embodiments disclosed herein overcome the aforementioned drawbacks by providing microspheres comprising a biodegradable and/or non-toxic (e.g. safe) simulant material made with non-biological DNA barcodes, and which can track and quantify indoor airflow. These disclosed microspheres (also referred to as microparticles) may simulate the aerosols comprising the air around us, and thus may help identify flow patterns. For example, the microspheres disclosed herein may be released in a facility/structure with one or more air-handling units to identify which of the units are functioning properly (e.g. collect and condition the air as desired). Such facilities may include, but are not limited to, a subway station, a train station, an airport, a corporate building, an office, convention centers, a warehouse, an apartment complex, a school, a home, an airplane, a submarine, or other similar facility/structure as would be understood by one having skill in the art upon reading the present disclosure.

Further, the potential for creating unique DNA barcodes is virtually unlimited, thus allowing for simultaneous and repeated releases of the microspheres comprising unique DNA barcodes, which dramatically reduces the costs associated with conducting source attribution testing for contaminants. For example a plurality of microspheres each of which comprise DNA barcodes different from one another can be released in the same and/or different areas of a facility and still be identified through their DNA bar codes. Moreover, use of microspheres comprising these DNA barcodes encapsulated in a carrier allow multiple releases to occur in a short time frame, in contrast to other conventional methods that require a cleanup of the facility between tests. Accordingly, use of the microspheres disclosed herein to conduct aerosol testing (e.g. to track particulate migration over a vast area for indoor testing) allows for the validation of models and aerosol detector locations that have previously been unobtainable.

According to one embodiment, a method of using the microspheres disclosed herein for indoor aerosol transport studies may include releasing a plurality of microspheres from a release location, collecting and/or detecting the microspheres at one or more collection locations, and analyzing the collected microspheres to identify the DNA barcodes encapsulated therein. In some approaches, a few, some, or all of the released microspheres may comprise DNA barcodes that are the same or different relative to each other. It is important to note that such a method is not limited to releasing microspheres at a single release location. For instance, in other approaches, microspheres may be released at two or more release locations, where some or all or the released microsphere may comprise the same or different DNA barcodes relative to each other.

In various approaches, the one or more collections locations may correspond to existing locations already having existing collection mechanisms/devices/detectors able to collect and/or detect the microspheres, such as a filter, a swab, etc. or other such mechanism/device as would be understood by one having skill in the art upon reading the present disclosure. In other approaches, the collection locations may be selected by a user and correspond to locations at which a user chooses to place/situate and/or install a collection mechanism/device/detector, etc. These collection locations may also be located at varying distances from the release location. For instance, microspheres may be detected several meters from the release point to more than 100 meters from the release point.

In further approaches, the plurality of collected microsphere may be analyzed in a polymerase chain reaction (PCR). PCR primers may be designed to only anneal to the DNA barcode of interest (e.g. the DNA barcode associated with the released microspheres) in order to avoid detecting any contaminant that is in the air, in preferred approaches. In even more approaches, the detected microspheres may be subject to additional analysis to determine, for example, the size (e.g. the aerodynamic diameter) of each microsphere, the number of copies of DNA barcode encapsulated in each microsphere, etc.

Figure 8:
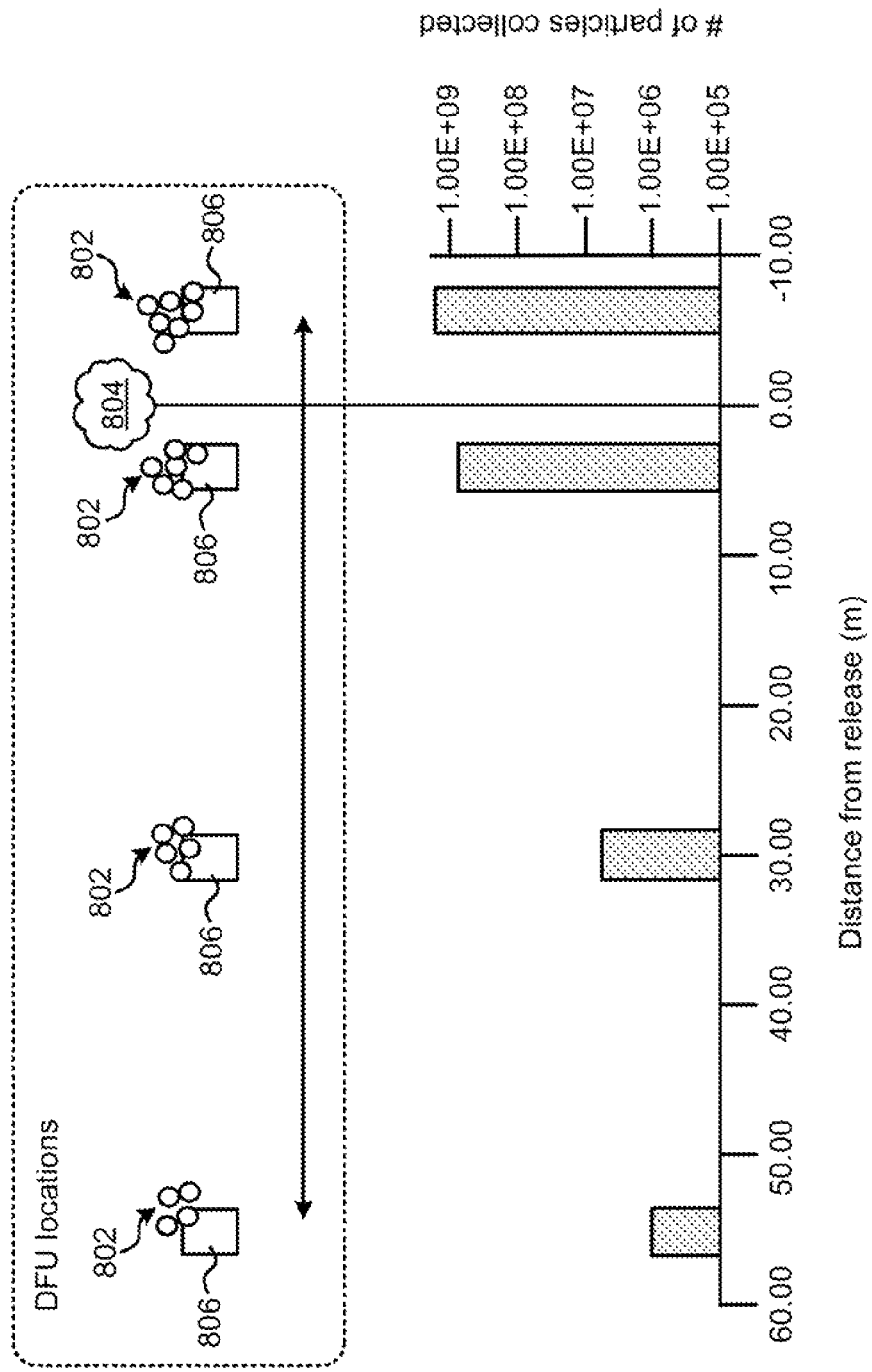
FIG. 8 illustrates data associated with the release of microspheres comprising a DNA barcode from a single location, according to one embodiment.

Reference is made to FIG. 8 which illustrates an exemplary experiment involving the tracking and quantification of particulate migration in an indoor environment using the microspheres disclosed herein. As shown in FIG. 8, a plurality of microspheres 802 comprising a carrier and a DNA barcode encapsulated in the carrier were released at the release location 802. In this exemplary experiment, each of the microspheres comprise the same DNA barcode.

As also shown in FIG. 8, the microspheres traveled varying distances from the release location 802 and were collected at four dry filter units (DFU) 806, each of which drew 800 L/min over two polyester filters. The collected microspheres were then processed and analyzed by PCR. The resulting particle count was based on the quantitative PCR analysis of the particles collected on the filters.

Figure 9:
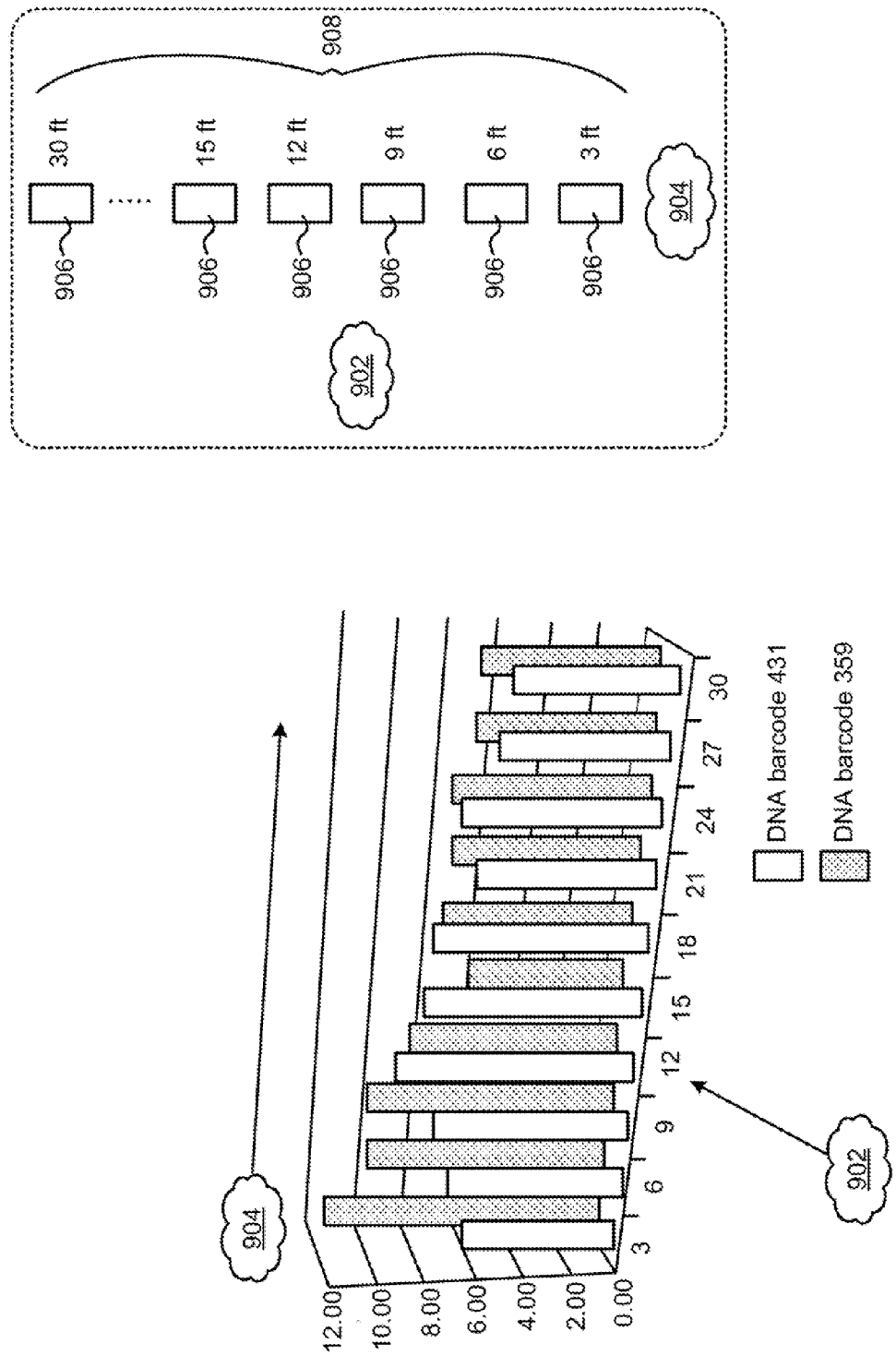
FIG. 9 illustrates data associated with the release of two sets of microspheres from two locations, where each set of microspheres comprises a unique DNA barcode, according to one embodiment.

Reference is now made to FIG. 9, which illustrates another exemplary experiment involving the simultaneous release of a first set and a second set of microspheres from two different release locations, where the first set of microspheres comprise a DNA barcode that is different from the DNA barcodes associated with second set of microspheres. For example, as shown in FIG. 9, the first set of microspheres comprise the DNA barcode labeled 431 and the second set of microspheres comprise the DNA barcode labeled 359. The first set of microspheres and the second set of microspheres were simultaneously released at a first release location 902 and a second release location 904, respectively. After the simultaneous release, the microspheres were collected on filters 906 and analyzed by PCR to identify which of the collected microspheres contained the DNA barcode 431 and which contained the DNA barcode 359.

As illustrated in the chart in FIG. 9, the microspheres comprising the DNA barcode 359 decreased in concentration as the distance from the release point increased. The microspheres comprising the DNA barcode 431 test particles, which were released and collected at 90 degrees to the sample collection layout 908, also decreased in concentration with distance.

The exemplary experiment shown in FIG. 9 clearly highlights the value of using microspheres with unique DNA barcodes for determining airflow based on different release locations, especially as compared to conventional products for airflow testing. For instance, where a conventional product is released from multiple locations, it is impossible to identify which of the detected particles (associated with the product) originated from a particular release location, as there is typically no distinguishing feature amongst the released particles.

A comparison between conventional aerosol transport testing materials and the microspheres comprising DNA barcodes described herein is provided in the table below.

| | Microspheres comprising DNA barcodes | GE Visolite Leak Detection System | Polymer Microspheres | SF$_6$ Industrial Gas | Traditional spores/ Commercial pesticide | Genetically modified spore (Not on the market) |
|---|---|---|---|---|---|---|
| Minimum time between releases | 0 | Days | Days to weeks | Days to weeks | Days to weeks | Days to weeks |
| Number of unique particles | Unlimited | 3 | Limited | 1 | Limited | Unlimited |
| Safety | Safe | Only improved for industrial air handlers | Hazardous | Environmentally unfriendly (powerful greenhouse gas) | Found in nature; possible contamination | Unknown |
| Ease of safety approval for aerosol | Easy | Limited | Limited | Easy | Easy | Unlikely |
| Diameter of test particle (μm) | .001-100 | n/a | 1-10 | $\sim 3 \times 10^{-4}$ | 0.5-4 | 0.5-4 |
| End-to-end cost for multiple releases | $ | $ | $$ | $ | $$$ | $$$$ |

As shown in the above table, the microspheres comprising DNA barcodes, such as those disclosed herein, offer several advantages over the conventional aerosol transport testing materials. For example, Visolite, produced by GE, has limited types of test materials and is not automatically approved for release in occupied facilities. In addition, polymer microspheres pose an inhalation hazard when released in large quantities and have a limited number of unique particle types. Moreover, spores, such as those that are used as a pesticide, also have limitations for release in public areas and are difficult to use for studies that require multiple releases. Moreover still, genetically modified spores will require extensive and repeated approval to satisfy public environmental concerns. Finally, the industrial gas sulfur hexafluoride ($SF_6$) has historically been used to study gas transport due to its easy-to-detect nature and low toxicity; however, $SF_6$ is a gas and does not accurately reproduce aerosol transport properties.

It is important to note, that embodiments of the present invention may also be used for aerosol transport studies in outdoor environments, as well. For instance, in one approach, the microspheres comprising the DNA barcodes disclosed herein may be released from an outdoor release location, and later collected and identified in order to determine the downwind spread of the microspheres. This may be particularly useful for meteorological studies involving the study of wind and outdoor airflow.

Source Attribution

In another approach, the microspheres disclosed herein may be used both to track the unwanted release of chemical/biological agents, and for source attribution. For example, releasing these microspheres from smoke stacks, mining operations or other industrial facilities may not only help assess the potential migration of greenhouse and other toxic gases (e.g. $CO_2$, $NO_x$, $SO_x$, $CH_4$, $N_2O$, $O_3$, CFCs, etc.), but also help identify which facilities are guilty of releasing said gases. Accordingly, companies and regulatory agencies can determine where effluents are likely to go, as well as the source of the effluents, by using the microspheres disclosed herein. Characterization of the airflow and source of these effluents will not only aid in emergency response from an unexpected release but can also help in false accusations of contamination.

Moreover, with the uniquely coded DNA, one could also apply these disclosed microspheres to oil and gas operations, fracking operations, etc. to better track fluid flow.

Response Training

The microspheres comprising the DNA barcodes disclosed herein may be used to evaluate and train individuals on how to respond to an incident. For instance, in one approach, these microspheres may be used to mimic smoke or other hazardous materials in an industrial setting. Accordingly, releasing these microspheres and studying their migration in such environments may help identify safe harbor sites and areas to avoid in an emergency. Using the microspheres in this manner would be particular useful to identify shelter areas in a mine fire or other facility where indoor is the preferable or only option in an emergency.

In another approach, the microspheres comprising the DNA barcodes disclosed herein may be used to evaluate decontamination protocols. For example, these microspheres may be dispersed on an individual and/or in an indoor or outdoor facility. After the clean-up/decontamination procedure is completed, the effectiveness of the procedure may be evaluated by determining how many of the microspheres were effectively and efficiently collected.

Validation of Diagnostic Tests

The microspheres comprising the DNA barcodes disclosed herein may be also be used to validate diagnostic tests; medical, environmental and bio-hazardous containment protocols; and/or various detectors (e.g. general aerosol detectors, bio detectors, etc.) in more approaches.

Identification Applications

The microspheres comprising the DNA barcodes disclosed herein may be additionally be used to tag an item for later identification. For instance, in one illustrative approach, these microsphere may be used essentially as a barcode to identify a package or other item.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims. Any of the methods, systems, devices, etc. described above, taken individually or in combination, in whole or in part, may be included in or used to make one or more systems, structures, etc. In addition, any of the features presented herein may be combined in any combination to create various embodiments, any of which fall within the scope of the present invention. Following are several examples of general and specific embodiments.

What is claimed is:

1. A product comprising:
a first carrier;
at least one fluorophore encapsulated in the first carrier; and
at least one DNA barcode encapsulated in the first carrier,
wherein the first carrier comprises a non-toxic material,
wherein the product is in an aerosol form and is biosafe,
wherein the non-toxic material is selected from a group consisting of: a vitamin, talc, an antacid, and combinations thereof.

2. The product as recited in claim 1, wherein the at least one DNA barcode has greater than or equal to about 80 bases to less than or equal to about 150 bases.

3. The product as recited in claim 1, wherein the first carrier has a diameter of about 1 nanometer to about 100 microns, and wherein the non-toxic material of the first carrier is water soluble.

4. The product as recited in claim 3, wherein the first carrier has a diameter in a range from greater than 10 microns to less than or equal to 100 microns.

5. The product as recited in claim 1, wherein the non-toxic material includes glucono-delta-lactone.

6. The product as recited in claim 1, wherein the product further comprises an additional material configured to alter one or more properties of the carrier, wherein the one or more properties of the carrier include a density, a morphology, a solubility, a charge, and a size, wherein the additional material is encapsulated in the first carrier.

7. A system, comprising:
the product as recited in claim 1;
a second carrier comprising a non-toxic material;
at least one fluorophore encapsulated in the second carrier; and
at least one DNA barcode encapsulated in the second carrier,
wherein the at least one DNA barcode encapsulated in the second carrier is different than the at least one DNA barcode encapsulated in the first carrier of the product.

8. A method of tracking and/or quantifying particulate migration outside of a human and/or animal body, comprising:
releasing the product as recited in claim 1 from one or more release locations;
collecting the product at one or more collection locations; and
analyzing the collected product to verify an identity, thereof.

9. The method as recited in claim 8, wherein the product is released from at least two different locations, and wherein the product is in an aerosol form.

10. The method as recited in claim 9, wherein the product further comprises:
a second carrier comprising a non-toxic material; and
at least one DNA barcode encapsulated in the second carrier,
wherein the at least one DNA barcode encapsulated in the second carrier is different than the at least one DNA barcode encapsulated in the first carrier,
wherein the location from which the second carrier is released is different than the location from which the first carrier is released.

11. A product comprising:
a first carrier;
at least one fluorophore encapsulated in the first carrier;
at least one DNA barcode encapsulated in the first carrier; and
an additional material selected from the group consisting of: an isotope marker, and a sunscreen composition, wherein the additional material is encapsulated in the first carrier,
wherein the first carrier comprises a non-toxic material,
wherein the product is in an aerosol form and is biosafe.

12. The product as recited in claim 11, wherein the non-toxic material is selected from a group consisting of: a food, a FDA approved food additive, a FDA approved color additive, and combinations thereof.

13. A method, comprising:
providing a first carrier, wherein the first carrier comprises a non-toxic material;
encapsulating at least one unique DNA barcode in the first carrier;
encapsulating at least one non-toxic fluorophore in the first carrier; and
aerosolizing the first carrier and the at least one non-toxic fluorophore and the at least one unique DNA barcode encapsulated therein,
wherein the non-toxic material is selected from a group consisting of: a vitamin, talc, an antacid, and combinations thereof.

14. A method, comprising:
providing a first carrier, wherein the first carrier comprises a non-toxic material;
encapsulating at least one unique DNA barcode in the first carrier;
encapsulating at least one non-toxic fluorophore in the first carrier;
aerosolizing the first carrier and the at least one non-toxic fluorophore and the at least one unique DNA barcode encapsulated therein; and
encapsulating at least one of an isotope marker and a sunscreen composition in the first carrier.

15. The method as recited in claim 14, wherein the non-toxic material is selected from a group consisting of: a food, an FDA approved food additive, a kosher certified food additive, a FDA approved color additive, and combinations thereof.

16. The method as recited in claim 14, wherein the carrier has a diameter in a range from greater than or equal to about 1 nanometer to less than 1 micron.

17. The method as recited in claim 14, further comprising:
providing a second carrier, wherein the second carrier comprises a second non-toxic material; and
encapsulating at least one unique DNA barcode in the second carrier, wherein the at least one unique DNA barcode encapsulated in the second carrier is different than the at least one unique DNA barcode encapsulated in the first carrier.

18. The method as recited in claim 14, wherein the carrier has a diameter of greater than 15 microns to less than or equal to about 100 microns.

* * * * *